United States Patent [19]

Kohn et al.

[11] Patent Number: 4,863,735
[45] Date of Patent: Sep. 5, 1989

[54] BIODEGRADABLE POLYMERIC DRUG DELIVERY SYSTEM WITH ADJUVANT ACTIVITY

[75] Inventors: Joachim B. Kohn, Highland Park, N.J.; Robert S. Langer, Somerville, Mass.; Steven M. Niemi, Sudbury, Mass.; James G. Fox, Littleton, Mass.

[73] Assignee: Massachusetts Institute of Technology, Cambridge, Mass.

[21] Appl. No.: 914,380

[22] Filed: Oct. 2, 1986

Related U.S. Application Data

[63] Continuation-in-part of Ser. No. 703,153, Feb. 19, 1985, Pat. No. 4,638,045.

[51] Int. Cl.[4] .......................... A61K 9/00; A61K 9/52; A61J 3/00
[52] U.S. Cl. ..................... 424/422; 424/426; 424/457; 424/458; 424/460; 424/461; 424/88; 424/89; 424/92; 424/78; 514/2; 514/8; 514/23; 514/885; 514/953; 514/963; 514/964; 514/965; 525/54.1
[58] Field of Search ............... 424/422, 426, 457, 458, 424/460–461, 218, 223, 88, 78, 89, 92; 514/885, 953; 604/891, 892, 894; 525/54.1

[56] References Cited

U.S. PATENT DOCUMENTS

| | | | |
|---|---|---|---|
| 3,773,737 | 11/1973 | Goodman et al. | 260/78 A |
| 4,225,581 | 9/1989 | Kreuter et al. | 424/89 |
| 4,258,029 | 3/1981 | Maloney et al. | 424/88 |
| 4,385,169 | 5/1983 | Kato et al. | 528/321 |
| 4,428,932 | 1/1984 | Overell | 424/91 |
| 4,450,150 | 5/1984 | Sidmon | 424/1.1 |
| 4,551,478 | 4/1985 | Nowinski et al. | 210/691 |
| 4,605,413 | 8/1986 | Urry et al. | 424/422 |
| 4,675,381 | 6/1987 | Bichon | 424/484 |
| 4,753,804 | 6/1988 | Iaccheri et al. | 424/489 |

FOREIGN PATENT DOCUMENTS

| | | | |
|---|---|---|---|
| 1138773 | 1/1983 | Canada | 167/135 |
| 0018189 | 10/1980 | European Pat. Off. | |
| 0064366 | 10/1982 | European Pat. Off. | |
| 0144314 | 8/1983 | Japan | 424/484 |
| 0202900 | 10/1985 | Japan | 424/484 |

OTHER PUBLICATIONS

Mozes et al, *PNAS* 77(8) 1980, pp. 4933–4937.
Preis and Langer, *J. Immunol. Methods*, 28, 193–197, (1979).
Langer, *Methods Enzymol.*, 73, 57–75 (1981).
Niemi, et al., *Lab. Animal Sci.*, 35, 609–612 (1985).
Wheeler, et al., *Int. Archs Allergy Appl. Immun.*, 69, 113–119 (1982).
Miller and Tees, *Clinical Allergy*, 4, 49–55 (1974).
Wheeler, et al., *Int. Archs Allergy Appl. Immun.*, 75, 294–299 (1984).
Penney, et al., *J. Biol. Stand.*, 13, 43–52 (1985).

*Primary Examiner*—Margaret Moskowitz
*Assistant Examiner*—Garnette D. Draper
*Attorney, Agent, or Firm*—Hamilton, Brook, Smith & Reynolds

[57] ABSTRACT

An antigen delivery system utilizing a biodegradable polymer with good mechanical properties in combination with a material stimulating the immune system. The material having adjuvant activity may be polymer degradation products or an adjuvant which is contained within or bound to the polymer. In one embodiment, the polymer is formed from tyrosine dipeptides. Poly(CTTH-iminocarbonate) is a preferred tyrosine dipeptide polymer for constructing implantable delivery systems for antigenic material. The polymer is not an adjuvant in itself but degrades into products which stimulate the immune system. The tyrosine dipeptide can also be used as a conventional adjuvant. The advantages of the system are that a polymer can be used to form a biodegradable integral structure which is useful as both an implantable source of an antigen or other biologically active compound and as a control means for the rate of release of the biologically active compound, wherein the result is sustained, relatively constant delivery of antigen with simultaneous stimulation of the immune response.

12 Claims, 2 Drawing Sheets

BIODEGRADABLE POLYMERIC DRUG DELIVERY SYSTEM WITH ADJUVANT ACTIVITY

REFERENCE TO RELATED APPLICATION

This application is a continuation-in-part application of U.S. patent application Ser. No. 703,153 filed Feb. 19, 1985 by Kohn et al. entitled "Novel Non-Peptide Polyaminoacid Bioerodible Polymers" now U.S. Pat. No. 4638045.

BACKGROUND OF THE INVENTION

The present invention is in the area of drug delivery and particularly in biodegradable, immunologically active, polymeric devices.

Many adjuvants such as aluminum oxide, polymethacrylate, surfactants, and incomplete Freund's adjuvant rely on a simple "depot" effect, releasing absorbed antigen over a short period of time, ranging from several hours to a maximum of a few weeks.

Recently, Preis and Langer, *J. Immunol. Methods* 28, 193 (1979); Langer, *Methods Enzymol.* 73, 57 (1981); and Niemi et al., *Lab. Animal Sci.* 35, 609 (1985), in an effort to extend the release time, have shown that a prolonged release of small amounts of antigen can be obtained using a polymeric antigen delivery device made of ethylene-vinyl acetate copolymer (EVAc). The prolonged release results in sustained production of serum antibodies over an extended period.

Although this antigen delivery system is an improvement over the prior art, the implanted device has to be surgically removed from the host after completion of the immunization process since EVAc is a nonbiodegradable polymer. It would be advantageous to use biodegradable devices for the controlled release of antigen to avoid this problem, especially in combination with a material having adjuvant activity. A particularly attractive concept is to intentionally design the polymer in such a way that its degradation products have adjuvant properties. This would make it possible to design a device capable of stimulating the immune response while simultaneously releasing antigen over prolonged periods of time.

It is therefore an object of the present invention to provide a polymeric material having adjuvant activity wherein a structure can be formed from the polymer for use in delivering relatively large amounts of a biologically active compound, especially an antigen.

It is a further object of the present invention to provide a material having adjuvant activity with sufficiently good mechanical properties, such as tensile strength, proccessibility and film and fiber formation, to be used as an implantable, controlled delivery device for biologically active compounds.

It is another object of the present invention to provide an implantable, controlled delivery device wherein the polymer degrades after implantation over a predetermined period of time so that surgical removal of the delivery device is not required but is possible during the delivery period, if desired.

SUMMARY OF THE INVENTION

The present invention is an implantable biodegradable polymeric device for controlled release of a biologically active compound in conjunction with a material which stimulates the immune system. The material having adjuvant activity may be a degradation product of the polymer or a compound which is dispersed within or bound to the polymer.

In the preferred embodiments, an antigen delivery system is formed of tyrosine dipeptides and polymers thereof. The tyrosine dipeptide polymers are particularly useful since they have good mechanical properties, including tensile strength, processibility and film and fiber formation, they degrade over time in vivo, and the degradation products stimulate an immune response.

It is highly desirable for the polymers to degrade over time so that surgical removal once all of the antigen is released is not required. By controlling the degree of polymerization, the quantity of polymer and antigen(s), the composition of the polymer, and the structure of the matrix (size, thickness, location, dispersion of the antigen throughout the polymer versus encapsulation of the antigen within the polymer matrix, etc), a system can be obtained which maximizes an immunological response to any antigen. A staggered immunological response can be produced by manipulating these same factors so that a portion of the antigen or a different antigen is released at a different time or at a different rate than the first antigen. Other biologically active compounds including immunomodulators (chemical agents which enhance or suppress an immune response), drugs, inorganic compounds, nucleic acids, lipids, and saccharides can also be dispersed and/or encapsulated within these devices. In the embodiments employing a material having adjuvant activity other than the polymer degradation products, any of the adjuvant materials known to those skilled in the art may be employed including tyrosine or tyrosine esters, muramyl dipeptide or Freund's adjuvant.

A preferred tyrosine dipeptide is the N- and C-terminal blocked N-Cbz-Tyr-Tyr-Hex (abbreviation: CTTH), which is polymerized to form a biodegradable polymer, poly(CTTH-iminocarbonate). The primary degradation product of this polymer is N-benzyloxycarbonyl-L-tyrosyl-L-tyrosine hexyl ester (CTTH). As shown by the following example using particulate suspensions, the degradation products of poly(CTTH-immunocarbonate) are as potent an adjuvant as complete Freund's adjuvant and muramyl dipeptide when the serum antibody response to bovine serum albumin (BSA) in male CD-1 mice is measured over 56 weeks. Further, BSA released from subcutaneously implanted polymeric antigen delivery devices made of poly(CTTH-iminocarbonate) results in significantly higher anti-BSA antibody titers than devices made of poly(Bisphenol A-iminocarbonate).

DETAILED DESCRIPTION OF THE INVENTION

The present invention is based on the discovery that tyrosine dipeptides and polymers thereof can be used to form biodegradable polymeric structures with good mechanical properties. The polymers have an additional advantage in that the degradation products are highly effective adjuvants. An adjuvant is an immunologically active substance which increases the immune response against a given antigen. Examples of adjuvants include tyrosine, muramyl dipeptide and Freund's adjuvent. Adjuvants are valuable in vaccination, allergy treatment and animal antibody production. Other polymeric devices which incorporate compounds with adjuvant activity may be formed using biodegradable polymers wherein the adjuvant is either dispersed within or encapsulated by the polymer or bound to the side chain of the polymer. Non-biodegradable polymers may also be useful in some situations.

The advantages of incorporating the adjuvant into the polymer and forming a device containing the antigen or other biologically active compound instead of injecting the adjuvant-antigen mixture directly or as a suspension of antigen-adjuvant particles include the higher loading capacity of the device, the prolonged release time, and the ability to remove the device if complications arise or it becomes desirable to do so for whatever reason. Another important advantage is that the device can be designed to release antigen at a controlled rate.

Figure 1:
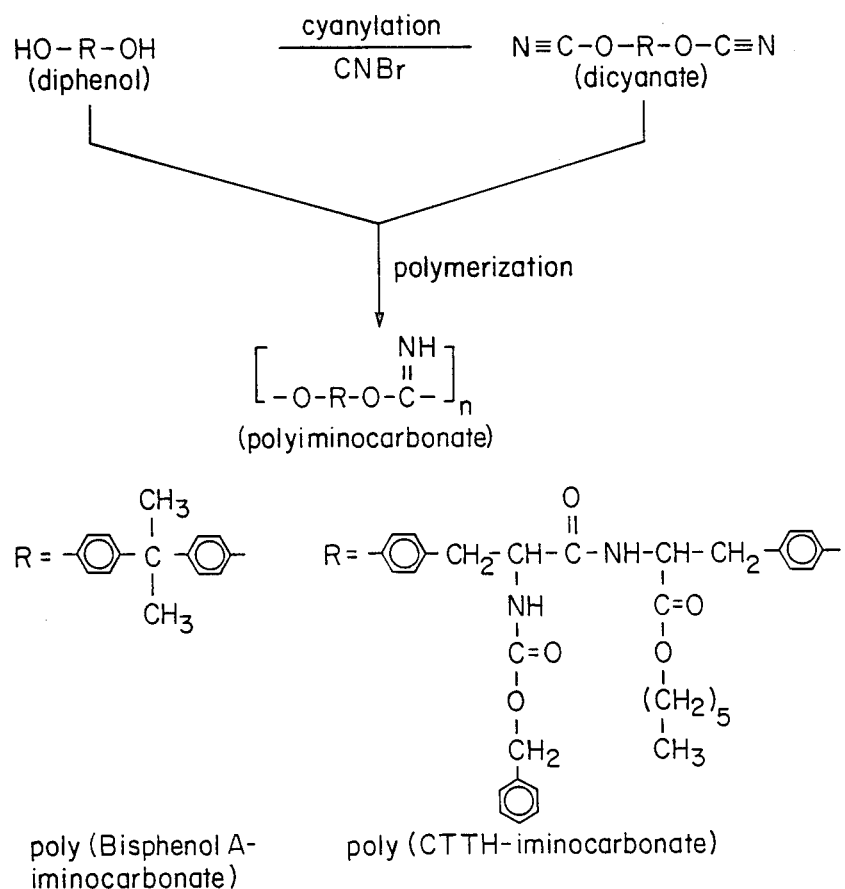
FIG. 1 is a synthetic pathway and molecular structures for poly(BPA-iminocarbonate) and poly(CTTH-iminocarbonate).

A preferred tyrosine dipeptide which has been discovered to have adjuvant activity is the N- and C-termini blocked N-Cbz-Tyr-Tyr-Hex(CTTH). The dipeptide is cyanylated and polymerized to form poly(CTTH-iminocarbonate). Poly(CTTH-iminocarbonate) (IUPAC nomenclature: poly[oxyimidocarbonyloxy-p-phenylene[2-hexyloxycarbonyl]ethylene]imino[2-[1-(benzyloxy)formamido]-1-oxotrimethylene]-p-phenylene]) is a structurally new, biodegradable polymer in which tyrosine dipeptide units are linked together by hydrolytically labile bonds via the tyrosine side-chain hydroxyl groups. The synthesis and structure of poly(CTTH-iminocarbonate) is shown in FIG. 1.

The synthesis and characteristics of related tyrosine dipeptide polymers such as CTTE is further described in U.S. patent application Ser. No. 703,153 filed Feb. 19, 1985 by Kohn et al. now U.S. Pat No. 4638045 entitled "Novel Non-Peptide Polyaminoacid Bioerodible Polymers". The synthesis of poly(CTTH-iminocarbonate), as described by J. Kohn and R. Langer in an article entitled "Polymerization Reaction Involving the Side Chains of α-L-Amino Acids" in *J. Amer. Chem. Soc.* (in press, 1986), is as follows:

L-tyrosine hexyl ester hydrochloride (Tyr-Hex.HCl)

Tyr-Hex.HCl is prepared by a modified version of the thionyl chloride technique: To n-hexanol (75 ml) at 0° C., thionyl choride (6.55 g, 0.055 mole), and L-tyrosine (9.05 g, 0.05 mole) is added. The resulting suspension is kept with stirring at 70° C. for 12 hr. Upon cooling Tyr-Hex.HCl precipitated. Precipitation is brought to completion by the addition of ether (350 ml). The precipitate is collected, washed with ether (3×100 ml) and dried. Yield: 94%; mp=162°-164° C.; Anal. ($C_{15}H_{24}ClNO_3$): C=59.83%, H=8.08%, N=4.58%, Cl=11.80%.

N-(N-benzyloxycarbonyl-L-tyrosyl)-L-tyrosine hexyl ester(Z-Tyr-Tyr-Hex, Comp. 3)

Z-Tyr-Tyr-Hex was prepared from Z-Tyr and Tyr-Hex.HCl by the carbodiimide coupling technique. Yield of crude product: 89%.

The crude material is purified by flash chromatography using (hexane:ethyl acetate:methanol)=(50:95:5) as mobile phase, followed by recrystallization: 1 g is dissolved at 50° C. in 10 ml of ethyl acetate:methanol=95:5. Then 20 ml hexane is added. After standing for 12 h at 25° C., the recrystallized material is collected and dried in vacuo. mp 154°-155° C., $[\alpha]20_D = +13.8°$ (C=5, ethyl acetate). IR (tetrachloroethane, cm$^{-1}$): $\gamma_{OH}$3580(m), $\gamma_{NH}$3409(m), $\gamma_{CH}$2957(m), 2930(m), 2859(w), $\gamma_{C=O}$ 1727(s), $\gamma_{amide}$ 1675(s), 1612(m), 1595 (weak), 1512(s), 1466(w), 1453(w), 1441(w), 1395(2), 1113, 1103 (w, doublet). Regions obscured by solvent absorptions: 3040-2960, 1300-1170, 1004-990, <860. Anal. ($C_{32}H_{38}N_2O_7$) C=68.35%, H=6.74%, N=5.01%.

Z-Tyr-Tyr-Hex-dicyanate (comp. 4)

The cyanylation procedure of Grigat and Pütter is extensively modified: Z-Tyr-Tyr-Hex (5 mmole, 2.81 g) and triethylamine (16 mmole, 2.2 ml) are dissolved in 15 ml THF (Solution A). Cyanogen bromide (19 mmole, 2.0 g) was dissolved in 20 ml THF (Solution B).

Under anhydrous conditions, solution B is placed into a 3-necked flask and cooled to −10° C. Solution A is placed into a dropping funnel and added to the reaction flash with vigorous stirring at a rate of 2 ml/min, keeping the reaction temperature below 0° C. A precipitate of Et$_3$N.HCl forms. Stirring is continued for an additional 15 min. During this time the reaction mixture is gradually warmed to +10° C. The precipitate was removed by filtration and washed with THF (30 ml). Combined filtrate and washings are cooled to 0° C., and ice-cold water (400 ml) is added with vigorous stirring resulting in a white precipitate of crude dicyanate. The crude product is collected, washed with (acetone:water)=(3:7) and dried. Crude product (1 g) is dissolved in boiling isopropanol (50 ml) and allowed to cool slowly. Fine needles precipitate. Yield: 78%, mp=152°-154° C. IR (tetrachloroethane, cm$^{-1}$): $\gamma_{NH}$ 3412(m), $\gamma_{CH}$ 2957(m), 2927(m), 2859(m), $\gamma_{OCN}$2279(s), 2262(s), 2239(s), $\gamma_{C=O}$1725(s, br), $\gamma_{amide}$1678(s), 1603(m), 1501(s).

Anal. ($C_{34}H_{36}N_4O_7$) C=66.60%, H=6.00%, N=9.09%.

Poly(Z-Tyr-Tyr-Hex-iminocarbonate) (comp. 5)

A solution of equimolar quantities of Z-Tyr-Tyr-Hex and Z-Tyr-Tyr-Hex-dicyanate was prepared in THF (0.2 mmole/ml), and placed in a sealed flask under an atmosphere of argon at 50° C. With stirring 0.1% (w/w) of K-t-butoxide (0.5M in t-butanol) is injected into the reaction mixture. The solution becomes viscous and after 90 min polymer precipitates. After 4 h the polymer is completely precipitated by addition of acetone, collected on a Buchner funnel, washed with acetone, and dried in vacuo. Yield: 90-95%. The progress of the polymerization reaction is followed by end group analysis employing the pyridine-barbituric acid color reaction for determination of cyanate esters.

Compound 5: IR (tetrachloroethane, cm$^{-1}$): $\gamma_{NH}$3412(m), 3332(2), $\gamma_{CH}$ 2958(m), 2928(m), 2859(w), $\gamma_{C=O}$ 1726(s, br), $\gamma_{amide}$ 2676(s, br, shoulder at 1690 (iminocarbonate)), $\gamma_{(aromatic\ ring)}$ 1603(w), 1502(w), 1310(s, br), 1056(m, br). Regions obscured by solvent absorptions: 3040-2960; 1300-1170; 1040-990; <860. $^1$H-NMR (CDCl$_3$) δ 0.88(3H, t, CH$_3$), 1.27(6H, m, narrow, 3CH$_2$), 1.56(2H, m, br, CH$_2$), 3.00(4H, m, br, 2CH$_2$), 4.05(2H, m, br, CH$_2$), 4.42(1H, m, br, CH), 4.78(1H, m, br, CH), 5.05(2H, s, CH$_2$), 5.55(2H, m, br, 2NH$_{amide}$), 6.57(1H, s, br, NH$_{imino}$), 7.08(8H, m, 2 1,4-Ph), 7.31(5H, m, Ph). Molecular weight (GPC and vapor pressure osmometry in chloroform): $M_n=11500$, $M_w=19500$, polydispersity=1.67, DP=19-20.

Anal. (calc. for $C_{33}H_{37}N_3O_7$: C=67.45%, H=6.35%, N=7.15%)
found: C=66.81%, H=6.57%, N=7.10%.

Poly(CTTH-iminocarbonate) has the following mechanical and chemical properties:
- appearance: slightly tinged, glassy
- softening point: 75°-85° C.
- melting range: 130°-140° C.
- thermal stability: degradation above 140° C.
- intrinsic viscosity: 0.27 (DMF, 25° C.)
- solubility: insoluble in water, alcohol, acetone, aromatic hydrocarbons, ether, hexane. Soluble in chlorinated hydrocarbons, THF, DMF, DMSO.
- polymer films: transparent, brittle
- molecular weight: 19,500

The effectiveness of a biodegradable implantable antigen delivery device with adjuvant activity is demonstrated by the following non-limiting example using a device formed of poly(CTTH-iminocarbonate) is outbred male CD-1 mice (Charles River Labatories, Kingston, N.Y.) immunized with BSA (Sigma, Lot A-7030, 50 microg per mouse). The adjuvant activity of CTTH is also clearly shown by comparison with known adjuvants, muramyl dipeptide (MDP, Calbiochem, Behring Diagnostics, 100 mg per mouse and Complete Freund's Adjuvant (CFA, Difco Laboratories, Detroit, MI; 1:1 emulsion).

L-tyrosine and its derivatives are known adjuvants, as reported by Wheeler et al., Archs. Allergy Appl. Immun. 69, 113 (1982); Wheeler et al., Int. Archs. Allergy Appl. Immum. 69, 113 (1984); Miller and Tees, Clinical Allergy 4, 49(1974); Moloney and Wojcik, Can. Pat. Appl. 325,670 (Apr. 18, 1979) and Eur. Pat. Appl. 18,189 (Oct. 29, 1980); Wheeler et al., Int. Archs. Allergy Appl. Immun. 75, 294 (1984); and Penney et al, J. Biol. Stand. 13, 43 (1985). Tyrosine esters, in particular, palmitoyl and stearyl esters, have been patented as adjuvants, U.S. Pat. No. 4,258,029; U.S. Pat. No. 4,428,932; and European Patent Application No. 0064366 (Nov. 10, 1982). In all of these references, the antigen is adsorbed onto the surface of the tyrosine particules which are then injected as a suspension.

For purposes of comparison of the adjuvant activity of tyrosine, tyrosine esters, and CTTH, particulate adjuvant suspensions were prepared from sieved particles (0 to 53 microns) of L-tyrosine (Chemalog, Chemical Dynamics Co.), dityrosine (Sigma), or CTTH (99% purity; Kohn, J. Am. Chem. Soc. 1986) as follows: to 400 mg of particles, 10 ml BSA solution (25 microg/mL in physiological saline) was added under sterile conditions. The vials were sealed and shaken for 12 hours to ensure complete adsorption of all BSA. BSA adsorption was confirmed by the procedure of Berg et al., Pharm. Ind. 48, 75, (1986). The sterility of all preparations was confirmed by incubating aliquats at 37° C. for 1 week in thioglycolate broth (Gibco, Grand Island, N.Y.).

Implantable antigen delivery devices were prepared by solvent casting using either poly(Bisphenol A-iminocarbonate), Mn=9,900, as described by Kohn in Biomaterials 7, 176 (1986), as a negative control, or poly(CTTH-iminocarbonate), Mn=9,900. One gram of polymer was dissolved in 15 ml chloroform:methylene chloride (1:1) and 110 mg sieved BSA particles (0 to 53 microns) were added. The mixture was extensively vortexed and poured into a Teflon-coated glass mold (5×5 cm). The mold was covered with sterile cloth and kept at room temperature for 2 days, followed by removal of residual solvent under high vacuum for 24 h. (24 h). Transparent, slightly brittle films containing 10% w/w of BSA were obtained.

Figure 2:
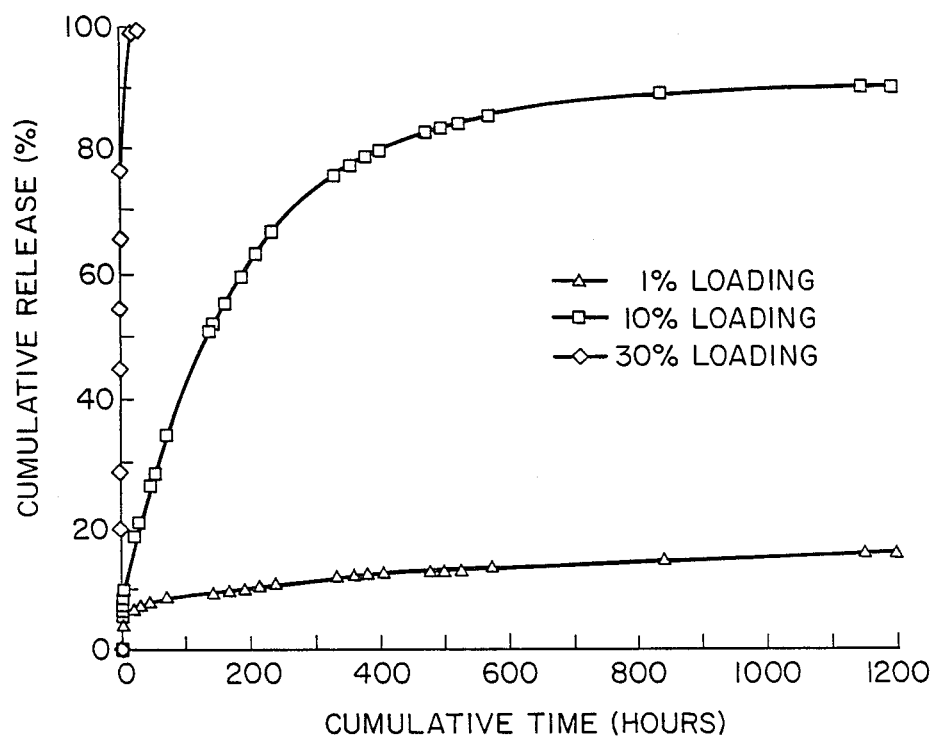
FIG. 2 is a graph of the in vitro cumulative release for Eosin Y from compression molded devices of poly(CTTH-iminocarbonate) as function of loading (1%, 10% and 30%) over time (hours).

Poly(L-tyrosine) was also considered for antigen delivery. Unfortunately, preliminary experiments showed that poly(L-tyrosine) is too biostable to be useful as an injectable or implantable adjuvant: subcutaneously injected particles of poly(L-tyrosine) persist as yellow, moderately inflamed patches for more than 56 weeks post injection. In contrast, poly(iminocarbonates) biodegrade within one year. Poly(CTTH-iminocarbonate) also has mechanical properties suitable for the formulation of drug delivery devices by solvent casting. By incorporating BSA, p-nitroaniline or Eosin Y into such polymeric devices, release for prolonged periods of time is observed, particularly at low loadings of 1 to 10% (w/w) as shown by FIG. 2.

For implantation, 0.5 mg portions of film were cut under sterile conditions. The animals were randomly divided into eight groups. Animals in groups A to F received a subcutaneous, primary injection at day 0, followed by an identical booster injection at day 2. The injections were 25 microgram BSA in 1 ml physiological saline solution (PSS) (Group A), 25 microgram BSA in 1 mL CFA (1:1 emulsion) (Group B), 25 microgram BSA+100 microgram MDP in 1 ml PSS (Group C), 25 microgram BSA adsorbed onto 40 mg of particulte tyrosine suspended in 1 ml of PSS (Group D), 25 microgram BSA adsorbed onto 40 mg particulate dityrosine in 1 mL of PSS (Group E), and 25 microgram BSA adsorbed onto 40 mg particulate CTTH in 1 ml of PSS (Group F). Single antigen delivery devices made of poly(BPA-iminocarbonate) or poly(CTTH-iminocarbonate) were implanted subcutaneously in the back of animals in Group G and H, respectively. No booster polymers were implanted. Blood samples were withdrawn from the retro-orbital plexus under ether anesthesia and heat fixed at 56° C. for 30 min. Sera were analyzed for anti-BSA antibody titers by the sheep red blood cell hemagglutination assay (Preis and Langer, J. Immunol. Meth. 28, 193 (1979). Hemagglutination titers were read after 24 hours. For each time point, the mean titer (2-fold dilutions) for each group was calculated. The means were then compared by a one way analysis of variance to determine statistical significance ($p<0.05$).

The results are shown in Table I.

TABLE I

Mean Hemagglutination anti-BSA Antibody Titers[a]

| Group | Adjuvant[f] | Antibody titers at week 2 | 4 | 6 |
|---|---|---|---|---|
| A[b] | — | 0.4 (0.20) | 0.9 (0.43) | 7.8 (1.25) |
| B[c] | CFA | 2.7 (0.38) | 4.6 (0.64) | 12.4 (0.57) |
| C[c] | MDP | 4.5 (0.30) | 5.7 (0.32) | 12.4 (0.48) |
| D[d] | Tyrosine | 1.5 (0.40) | 3.0 (0.65) | 12.9 (0.62) |
| E[d] | Dityrosine | 2.5 (0.19) | 4.2 (0.52) | 11.4 (0.30) |
| F[d] | CTTH | 1.9 (0.35) | 4.1 (0.55) | 12.1 (0.42) |
| G[e] | poly(BPA-iminocarbonate) | 0.6 (0.25) | 2.2 (0.65) | 2.0 (0.59) |
| H[e] | poly(CTTH-iminocarbonate) | 2.3 (0.43) | 6.1 (0.79) | 5.9 (0.77) |
| Group | Adjuvant[b] | 8 | 12 | 16 |
| A[b] | — | 7.9 (1.12) | 7.8 (1.17) | 7.7 (1.21) |
| B[c] | CFA | 11.4 (0.59) | 10.8 (0.48) | 10.1 (0.37) |
| C[c] | MDP | 12.5 (0.45) | 11.4 (0.22) | 11.1 (0.23) |
| D[d] | Tyrosine | 11.6 (0.32) | 11.7 (0.39) | 11.0 (0.30) |
| E[d] | Dityrosine | 11.6 (0.35) | 11.3 (0.26) | 11.3 (0.21) |

TABLE I-continued

| | Mean Hemagglutination anti-BSA Antibody Titers[a] | | | |
|---|---|---|---|---|
| F[d] | CTTH | 11.2 (0.30) | 11.1 (0.27) | 11.0 (0.55) |
| G[e] | poly(BPA-iminocarbonate) | 3.7 (0.72) | 4.5 (0.99) | 5.3 (0.99) |
| H[e] | poly(CTTH-iminocarbonate) | 7.4 (0.29) | 9.2 (0.41) | 9.3 (0.39) |
| Group | Adjuvant[b] | | 24 | 56 |
| A[b] | — | | 5.8 (1.12) | 2.5 (1.00) |
| B[c] | CFA | | 9.4 (0.67) | 6.2 (0.79) |
| C[c] | MDP | | 9.1 (0.46) | 5.8 (1.27) |
| D[d] | Tyrosine | | 9.9 (0.65) | 5.9 (1.17) |
| E[d] | Dityrosine | | 9.2 (0.32) | 5.7 (1.07) |
| F[d] | CTTH | | 9.8 (1.18) | 7.1 (1.37) |
| G[e] | poly(BPA-iminocarbonate) | | 3.6 (1.06) | 4.1 (0.83) |
| H[e] | poly(CTTH-iminocarbonate) | | 8.6 (0.28) | 5.1 (0.69) |

[a]Titers represent 2-fold dilutions and are expressed as $-\log_2 \times 10$. Data represent the arithematic mean for 5 to 10 identically treated animals. Parentheses show the standard error of the mean.
[b]Negative control, booster administered at week 4.
[c]Positive control, booster administered at week 4.
[d]Injectable suspensions of particular adjuvant. Antigen was physically adsorbed onto the surface. Booster administered at week 4.
[e]Implantable, polymeric antigen delivery systems. No booster administered.
[f]In all groups, the total dose of antigen was 50 microg BSA per animal. Total adjuvant doses per animal were: 200 mg MDP, 80 mg of particles in Groups D, E, F, and 0.45 mg in Groups G and H.

Table I shows the mean hemagglutination titers for anti-BSA antibodies obtained for each of the experimental groups. No statistically significant differences were obtained among the various tyrosine derivatives themselves or when comparing the results obtained for CFA or MDP. With the exception of week 56, throughout the entire course of the experiment the mean anti-BSA antibody titers in the animals treated with poly(CTTH-iminocarbonate) implants were significantly higher ($p<0.006$) than the titers in the animals treated with poly(Bisphenol A-iminocarbonate) implants.

It is evident that all tested tyrosine derivatives, including tyrosine dipeptides, act as potent adjuvants, equivalent to CFA, when BSA is physically adsorbed onto the surface of particles. Heretofore, only simple derivatives of tyrosine have been examined for their adjuvanticity.

Since the two types of implants were fabricated in an identical fashion, contained an identical dose of antigen, were shown to have comparable release profiles in vitro (Kohn, Biomaterials 7, 176, 1986), and share the same iminocarbonate backbone structure, the observed higher antibody titers obtained for poly(CTTH-iminocarbonate) can conceivably be attributed to an intrinsic adjuvanticity of CTTH, its monomeric repeat unit.

Considering that a total dose of 80 mg of adjuvant was used in Groups D, E, and F, versus 0.45 mg for the implanted devices (Groups G and H), the antibody titers obtained for CTTH (Group F) and poly(CTTH-iminocarbonate) (Group H) cannot be compared directly. The choice of such a small device was initially dictated by the necessity to have rather high loadings of antigen (10% w/w) in order to achieve substantial antigen release rates (FIG. 2). A larger device, containing more adjuvant, may result in even higher antibody titers.

With the termination of the experiment at week 56, all animals were euthanized and the injection or implantation sites were examined. In none of the animals of Group D (tyrosine particles), Group E (dityrosine particles) or Group F (CTTH particles) was it possible to detect any residues of the injected particulate materials. None of the animals showed any tissue abnormality. Their injection sites were indistinguishable from the injection sites of saline treated mice (Group A). As expected, large white nodules, filled with a creamy, pus-like material were found at the injection site of all animals of Group B (Complete Freund's Adjuvant). Histological examination revealed the typical lipogranulomatous inflammatory response commonly associated with Complete Freund's Adjuvant.

In most animals implanted with polymeric devices made of poly(BPA-iminocarbonate) (Group G) or poly(CTTH-iminocarbonate) (Group H), small amounts of polymeric residues could be detected at the implantation site. However, no gross pathological changes were evident from visual inspection of these sites. Histological examination showed that the polymeric implants were surrounded by a thin layer of fibrous connective tissue that ranged from 1 to 3 cells in thickness. The majority of implants were localized to the subcutis but in a few instances seemed to have gravitated into the dermis. Tissue response did not vary with location. The presence of a few lymphocytes and macrophages and almost complete absence of polymorphonuclear leukocytes either within or adjacent to the connective tissue layer indicated a very mild chronic inflammatory response to these implants. No significant difference in the intensity of the tissue reaction towards poly(CTTH-iminocarbonate) implants or poly(BPA-iminocarbonate) implants was evident. Hence it seems that the observed higher antibody titers for poly(CTTH-iminocarbonate) implants were not caused by the immunostimulatory effect of a strong local inflammatory response to the implant material itself.

In conclusion, the controlled release of antigen from a biodegradable antigen delivery device which degrades into a material with adjuvant properties results in higher antibody titers than anitgen release from a very similar device made of a material with no adjuvant properties. Accordingly, biodegradable antigen delivery systems may be designed which have adjuvanticity in addition to serving as a repository for antigen.

This approach may be used in the development of a procedure for the induction of long-lasting immunization with a single administration of antigen. In particular, the tyrosine dipeptides, in conjunction with antigen or as polymers combined with antigens, can be optimized to produce release of antigen at a rate designed to maximize immunological response or to produce a staggered release. Classically, maximum response to an antigen is achieved by multiple exposure to the antigen. This may be expensive or impossible in some situations, such as in third world countries where the people or animals to be innoculated are in remote areas. The present invention allows one to implant a single device which may contain one or more antigens for release at the appropriate times. Not only does this method provide for staggered release of the same antigen, but may also avoid the problem of not achieving the desired immunological response to multiple antigens when they are given in combination.

The disclosed tyrosine dipeptides are multipurpose: they have adjuvanticity properties and they can be used to form polymers which are biodegradable into products that stimulate an immunologic response. The polymers have desirable mechanical properties for forming controlled drug release devices according to the present invention.

Modifications and variations of the present invention, tyrosine dipetides and polymers thereof for use as adjuvants and controlled release, biodegradable drug delivery systems, will be obvious to those skilled in the art. Such modifications and variations are intended to come within the scope of the appended claims.

We claim:

1. An implantable, polymeric device for delivery of biologically active compounds, said device comprising at least one biologically active compound and a biodegradable, tyrosine dipeptide polymer said polymer degrading to form a product having adjuvant activity for said biologically active compound.

2. The device of claim 1 further comprising an additional material having adjuvant activity for said biologically active compound, said additional material being chemically bound to the tyrosine dipeptide polymer forming the device.

3. The device of claim 1 wherein the tyrosine dipeptide polymer having adjuvant activity is a degradation product of the biodegradable polymer forming the device.

4. The device of claim 1 wherein said tyrosine dipeptide polymer is selected from the group consisting of poly(CTTH-iminocarbonate) and poly(CTTE-iminocarbonate).

5. The device of claim 1 wherein said polymers are chemically structured to degrade over a specific period of time.

6. The device of claim 1 wherein said tyrosine dipeptide polymer encapsulates the biologically active compound.

7. The device of claim 1 wherein the biologically active compound is dispersed within the tyrosine dipeptide polymer.

8. The device of claim 1 wherein said biologically active compound is selected from the group consisting of antigens, immunomodulators, drugs, inorganic compounds, nucleic acids, lipids and saccharides.

9. The device of claim 1 wherein the tyrosine dipeptide polymer further encapsulates a material having adjuvant activity for said biologically active compound, said material being selected from the group consisting of complete Freund's adjuvant, muramyl acid, and tyrosine and tyrosine derivatives.

10. A biodegradable device for the controlled release of at least one biologically active compound, said device comprising a tyrosine dipeptide polymer and at least one biologically active compound, which device, when implanted into a host, controllably releases the biologically active compound while simultaneously degrading to form a compound having adjuvant activity for the controllably released, biologically active compound.

11. A biodegradable device as in claim 10 further containing therein an additional material having adjuvant activity.

12. A biodegradable device as in claim 11 wherein said additional material is selected from the group consisting of Freund's adjuvant, muramyl acid, tyrosine and tyrosine derivatives.

* * * * *

UNITED STATES PATENT AND TRADEMARK OFFICE
CERTIFICATE OF CORRECTION

PATENT NO. : 4,863,735

DATED : September 5, 1989

INVENTOR(S) : Joachim B. Kohn, Robert S. Langer, Steven M. Niemi & James G. Fox

It is certified that error appears in the above-identified patent and that said Letters Patent is hereby corrected as shown below:

Column 1, line 4, insert:

---GOVERNMENT SUPPORT

The invention described herein was supported in whole or in part by the National Institute of Health.---

Signed and Sealed this

Eleventh Day of December, 1990

Attest:

HARRY F. MANBECK, JR.

Attesting Officer

Commissioner of Patents and Trademarks